(12) United States Patent
Hibbard et al.

(10) Patent No.: US 11,386,557 B2
(45) Date of Patent: Jul. 12, 2022

(54) SYSTEMS AND METHODS FOR SEGMENTATION OF INTRA-PATIENT MEDICAL IMAGES

(71) Applicant: Elekta, Inc., Atlanta, GA (US)

(72) Inventors: Lyndon Stanley Hibbard, St. Louis, MO (US); Xiao Han, Chesterfield, MO (US)

(73) Assignee: Elekta, Inc., Atlanta, GA (US)

( * ) Notice: Subject to any disclaimer, the term of this patent is extended or adjusted under 35 U.S.C. 154(b) by 72 days.

(21) Appl. No.: 16/949,648

(22) Filed: Nov. 9, 2020

(65) Prior Publication Data

US 2021/0056687 A1    Feb. 25, 2021

Related U.S. Application Data

(63) Continuation of application No. 16/201,620, filed on Nov. 27, 2018, now Pat. No. 10,867,385, which is a
(Continued)

(51) Int. Cl.
     *G06K 9/00*      (2022.01)
     *G06T 7/00*      (2017.01)
     (Continued)

(52) U.S. Cl.
     CPC ............ *G06T 7/0012* (2013.01); *A61B 6/032* (2013.01); *A61B 6/5294* (2013.01);
     (Continued)

(58) Field of Classification Search
     CPC ... G06T 7/0012; G06T 2210/41; G06T 17/00; G06T 2207/30004; G06T 2207/10081;
     (Continued)

(56) References Cited

U.S. PATENT DOCUMENTS

| | | |
|---|---|---|
| 6,549,646 B1 | 4/2003 | Yeh et al. |
| 8,953,856 B2 * | 2/2015 | Ostrovsky-Berman ...................... G06T 7/35 382/128 |

(Continued)

FOREIGN PATENT DOCUMENTS

| | | |
|---|---|---|
| AU | 2017209046 A1 | 7/2018 |
| CN | 102239495 A | 11/2011 |

(Continued)

OTHER PUBLICATIONS

U.S. Appl. No. 15/385,732 U.S. Pat. No. 10,169,871 Dec. 20, 2016 Systems and Methods for Segmentation of Intra-Patient Medical Images.

(Continued)

*Primary Examiner* — Shervin K Nakhjavan
(74) *Attorney, Agent, or Firm* — Schwegman Lundberg & Woessner, P.A.

(57) ABSTRACT

Embodiments disclose a method and system for segmenting medical images. In certain embodiments, the system comprises a database configured to store a plurality of medical images acquired by an image acquisition device. The plurality of images include at least one first medical image of an object, and a second medical image of the object, each first medical image associated with a first structure label map. The system further comprises a processor that is configured to register the at least one first medical image to the second medical image, determine a classifier model using the registered first medical image and the corresponding first structure label map, and determine a second structure label map associated with the second medical image using the classifier model.

20 Claims, 7 Drawing Sheets

Related U.S. Application Data continuation of application No. 15/385,732, filed on Dec. 20, 2016, now Pat. No. 10,169,871.

(60) Provisional application No. 62/281,652, filed on Jan. 21, 2016.

(51) Int. Cl.
| | | |
|---|---|---|
| *G06K 9/62* | (2022.01) | |
| *G06T 7/30* | (2017.01) | |
| *G06T 7/11* | (2017.01) | |
| *G06T 7/143* | (2017.01) | |
| *G06V 30/194* | (2022.01) | |
| *G06T 7/38* | (2017.01) | |
| *A61B 6/03* | (2006.01) | |
| *A61B 6/00* | (2006.01) | |

(52) U.S. Cl.
CPC ......... *G06K 9/6254* (2013.01); *G06K 9/6256* (2013.01); *G06K 9/6267* (2013.01); *G06T 7/11* (2017.01); *G06T 7/143* (2017.01); *G06T 7/30* (2017.01); *G06T 7/38* (2017.01); *G06T 7/97* (2017.01); *G06V 30/194* (2022.01); *G06T 2207/20084* (2013.01); *G06T 2207/20128* (2013.01); *G06T 2207/30004* (2013.01); *G06T 2207/30081* (2013.01); *G06V 2201/031* (2022.01)

(58) Field of Classification Search
CPC ........... G06T 7/174; G06T 2207/20084; G06T 2207/20224; G16H 30/40; G16H 50/30; G06K 2209/05; G06K 9/6267; G06K 9/6201

See application file for complete search history.

(56) References Cited

U.S. PATENT DOCUMENTS

| | | | |
|---|---|---|---|
| 9,092,691 B1* | 7/2015 | Beaumont | G06T 7/0014 |
| 10,169,871 B2 | 1/2019 | Hibbard et al. | |
| 2002/0052875 A1* | 5/2002 | Smith | G06F 16/40 |
| | | | 718/1 |
| 2003/0174872 A1* | 9/2003 | Chalana | G06K 9/00 |
| | | | 382/128 |
| 2008/0292194 A1* | 11/2008 | Schmidt | G06T 7/143 |
| | | | 382/131 |
| 2009/0226060 A1* | 9/2009 | Gering | G06T 7/174 |
| | | | 382/128 |
| 2010/0266170 A1 | 10/2010 | Khamene et al. | |
| 2011/0052018 A1* | 3/2011 | Blaffert | G06T 7/149 |
| | | | 382/128 |
| 2011/0179044 A1* | 7/2011 | Crum | G06K 9/6224 |
| | | | 707/E17.014 |
| 2012/0008838 A1* | 1/2012 | Guyon | G16H 50/20 |
| | | | 382/128 |
| 2012/0177263 A1* | 7/2012 | Akinyemi | G06T 7/11 |
| | | | 382/128 |
| 2012/0207359 A1* | 8/2012 | Konukoglu | G06K 9/6277 |
| | | | 382/128 |
| 2013/0336553 A1 | 12/2013 | Buisseret et al. | |
| 2014/0247977 A1* | 9/2014 | Han | G06T 7/12 |
| | | | 382/159 |
| 2015/0161786 A1* | 6/2015 | Seifert | G06T 7/149 |
| | | | 382/119 |
| 2015/0178938 A1* | 6/2015 | Gorman, III | G06T 7/174 |
| | | | 382/131 |
| 2015/0238148 A1 | 8/2015 | Georgescu et al. | |
| 2015/0356367 A1 | 12/2015 | Han | |
| 2016/0117818 A1* | 4/2016 | Park | A61B 5/7425 |
| | | | 382/131 |
| 2016/0300120 A1* | 10/2016 | Haas | G06T 7/11 |
| 2016/0328855 A1* | 11/2016 | Lay | G06T 5/005 |
| 2017/0116744 A1* | 4/2017 | Abedini | G06V 10/42 |
| 2017/0213339 A1 | 7/2017 | Hibbard et al. | |
| 2017/0337682 A1* | 11/2017 | Liao | G06T 7/0012 |
| 2018/0168780 A1* | 6/2018 | Kopelman | A61C 5/44 |
| 2019/0108635 A1 | 4/2019 | Hibbard et al. | |

FOREIGN PATENT DOCUMENTS

| | | |
|---|---|---|
| CN | 102737379 A | 10/2012 |
| CN | 103069455 A | 4/2013 |
| CN | 105765629 A | 7/2016 |
| CN | 106062782 A | 10/2016 |
| CN | 109074500 A | 12/2018 |
| JP | 2002330951 A | 11/2002 |
| JP | 2010504578 A | 2/2010 |
| JP | 2012030072 A | 2/2012 |
| JP | 2013506478 A | 2/2013 |
| JP | 2015036123 A | 2/2015 |
| WO | WO-2007029467 A1 | 3/2007 |
| WO | WO-2017127439 A1 | 7/2017 |

OTHER PUBLICATIONS

U.S. Appl. No. 16/201,620 U.S. Pat. No. 10,867,385 Nov. 27, 2018 Systems and Methods for Segmentation of Intra-Patient Medical Images.

U.S. Appl. No. 16/201,620, filed Nov. 27, 2018 Systems and Methods for Segmentation of Intra-Patient Medical Images.

"European Application Serial No. 17703003.8, Communication Pursuant to Article 94(3) EPC dated Nov. 9, 2021", 5 pgs.

"U.S. Appl. No. 15/385,732, Non Final Office Action dated Jun. 14, 2018", 15 pgs.

"U.S. Appl. No. 15/385,732, Notice of Allowance dated Oct. 31, 2018", 11 pgs.

"U.S. Appl. No. 15/385,732, Response filed Sep. 14, 2018 to Non Final Office Action dated Jun. 14, 2018", 8 pgs.

"U.S. Appl. No. 16/201,620, Non Final Office Action dated May 1, 2020", 16 pgs.

"U.S. Appl. No. 16/201,620, Notice of Allowance dated Aug. 19, 2020", 8 pgs.

"U.S. Appl. No. 16/201,620, Response filed Aug. 3, 2020 to Non Final Office Action dated May 1, 2020", 7 pgs.

"Australian Application Serial No. 2017209046, First Examination Report dated Feb. 27, 2020", 3 pgs.

"Australian Application Serial No. 2017209046, Response filed Apr. 16, 2020 to First Examination Report dated Feb. 27, 2020", 22 pgs.

"Australian Application Serial No. 2017209046, Response filed May 7, 2020 to Subsequent Examiners Report dated Apr. 22, 2020", 45 pgs.

"Australian Application Serial No. 2017209046, Subsequent Examiners Report dated Apr. 22, 2020", 3 pgs.

"Chinese Application Serial No. 201780007353.6, Office Action dated Jul. 3, 2019", W/English Translation, 15 pgs.

"Chinese Application Serial No. 201780007353.6, Response filed Nov. 18, 2019 to Office Action dated Jul. 3, 2019", w/ English claims, 5 pgs.

"European Application Serial No. 17703003.8, Communication Pursuant to Article 94(3) EPC dated Mar. 24, 2020", 6 pgs.

"European Application Serial No. 17703003.8, Response filed Mar. 8, 2019 to Office Action dated Aug. 31, 2018", 21 pgs.

"European Application Serial No. 17703003.8, Response filed Oct. 1, 2020 to Communication Pursuant to Article 94(3) EPC dated Mar. 24, 2020", 12 pgs.

"International Application Serial No. PCT/US2017/013962, International Preliminary Report on Patentability dated Aug. 2, 2018", 10 pgs.

"International Application Serial No. PCT/US2017/013962, International Search Report dated Mar. 28, 2017", 4 pgs.

"International Application Serial No. PCT/US2017/013962, Written Opinion dated Mar. 28, 2017", 8 pgs.

"Japanese Application Serial No. 2018-538580, Office Action dated Mar. 10, 2020", w/ English translation, 5 pgs.

(56) References Cited

OTHER PUBLICATIONS

"Japanese Application Serial No. 2018-538580, Response filed Jun. 5, 2020 to Office Action dated Mar. 10, 2020", w/ English claims, 14 pgs.

Sharma, Neeraj, et al., "Automated medical image segmentation techniques", Journal of Medical Physics, vol. 35, No. 1, (Jan. 7, 2010), 3 pgs.

* cited by examiner

SYSTEMS AND METHODS FOR SEGMENTATION OF INTRA-PATIENT MEDICAL IMAGES

CROSS REFERENCE TO RELATED APPLICATION

This application is a continuation of and claims the benefit of priority to U.S. application Ser. No. 16/201,620, filed Nov. 27, 2018, which is a continuation of and claims the benefit of priority to U.S. application Ser. No. 15/385,732, filed Dec. 20, 2016, which claims the benefit of priority to U.S. Provisional Application No. 62/281,652, filed on Jan. 21, 2016, the entire contents of which are incorporated herein by reference in their entireties.

TECHNICAL FIELD

This disclosure relates generally to image segmentation. More specifically, this disclosure relates to systems and methods for accurate medical image segmentation using a patient's prior image information to aid in the segmentation of the patient's succeeding images.

BACKGROUND

Image segmentation techniques are widely used for segmenting medical images and determining contours between anatomical structures within the images. For example, in radiation therapy, automatic segmentation of organs is usually performed to reduce contouring time, and improve contour accuracy and consistency over various hospitals. However, automated segmentation of images remains to be a very difficult task due to noises, limited image contrast and/or low image quality. For example, medical images having lower image quality, such as some computer tomography (CT) or cone-beam computer tomography (CBCT) images that may be used to treat cancer patients, are known to have lower contrast and little texture for most soft tissue structures. Therefore, conventional image segmentation methods based primarily on image contrast often fail to find an accurate contour between the background and anatomical structures (e.g., organs or tumors) of interest, or between different anatomical structures in a medical image.

Two main methods of medical image segmentation include Atlas-based auto-segmentation and statistical learning segmentation. Atlas-based auto-segmentation (ABAS) registers an anatomy labeled image onto an unlabeled image and transfers the labels, wherein the labels identify the anatomic structures in the images (e.g., prostate, bladder, rectum and the like). Statistical learning segmentation classifies image voxels according to the voxel properties of the anatomic structures in the images, wherein the voxel properties include, for example, intensity, texture features and the like.

FIG. 1 illustrates an exemplary three-dimensional (3D) CT image from a typical prostate cancer patient. Illustration (A) shows a pelvic region of the patient in a 3D view, which includes the patient's bladder, prostate, and rectum. Images (B), (C), and (D) are axial, sagittal and coronal views from a 3D CT image of this pelvic region. As shown in images (B), (C), and (D), most part of the patient's prostate boundary is not visible. That is, one cannot readily distinguish the prostate from other anatomical structures or determine a contour for the prostate. In comparison, images (E), (F), and (G) show the expected prostate contour on the same 3D CT image. As illustrated in FIG. 1, conventional image segmentation methods based solely on contrast and textures presented in the image would likely fail when used to segment this exemplary 3D CT image.

Recent developments in machine learning techniques make improved image segmentation on lower quality images possible. For example, supervised learning algorithms can "train" computers to predict the anatomical structure each pixel or voxel of a medical image represents. Such prediction usually uses features of the pixel or voxel as inputs. Therefore, the performance of the segmentation highly depends on the type of features available. To date, most learning-based image segmentation methods are based primarily on local image features such as image intensities and image textures. As a result, these segmentation methods are still suboptimal for lower quality images, such as the 3D CT image shown in FIG. 1.

Accurate segmentation of anatomical structures from CT images remains a challenging problem. Segmented serial images of the same patient have a special utility in adaptive plan review/re-planning and dose accumulation. Serial images necessarily sample different probability distributions than those of populations and therefore ought to provide information that aids the segmentation of new serial images.

Some methods propose combining atlas and statistical methods to gain improved segmentation accuracy. For example, one method bases its on-line learning and patient-specific classification on location-adaptive image contexts. The location-adaptive classifiers are trained on static image appearance features and image context features as well. Such a method has been used on serial prostate images with the stated goal of refining the patient's prostate segmentation as radiotherapy progressed. However, it requires that the data be treated as a three-dimensional data object using the spatial distribution of the voxel patch-pairs as features themselves, and in addition, using a random forest (RF) method.

Alternatively, another method proposes combining bladder volume metric and landmark locations with conventional deformable registration in a study of atlas based segmentation of serial CT images of the cervix-uterus. However, the method can be computationally expensive and error prone since use of landmarks requires human intervention.

Furthermore, another method uses random forests for brain tissue segmentation (in a semi-supervised learning mode) such that the decision forest is trained on anatomy-labeled pre-surgical imagery and unlabeled post-surgical images of the same patient. However, this approach avoids the registration step and thus, fails to take advantage of useful information in Atlas-based registration.

In addition, random forest segmentation has been combined with image registration to perform image segmentation. This allows for inter-patient segmentation, and through the mechanism of an "atlas forest", multiple patients' images were registered to a common coordinate frame, with one image per forest model. However, the method requires different compositions of training data to provide resulting models.

Further, methods combining deformable registration and random forests are used to segment the bones of the face and teeth from dental Cone Beam CT images Patient images are registered to an atlas for an initial prediction or estimate of the segmentation. This is followed by a sequence of random forest classifiers that use context features as part of the features to be trained on at each stage of the sequence. However, to the method requires using deformable registration and RF classifiers to form RF models based on prior images of the same patient.

The disclosed methods and systems are designed to solve one or more problems discussed above, by combining Atlas-based segmentation and statistical learning, combining population with intra-patient image and structure information, and enabling convenient updating of a patient segmentation model in order to improve segmentation performance on medical images in radiation therapy or related fields.

SUMMARY

Certain embodiments of the present disclosure relate to a system for segmenting medical images. The system may include a database configured to store a plurality of medical images acquired by an image acquisition device. The plurality of medical images may include at least one first medical image of an object, and a second medical image of the object, each first medical image associated with a first structure label map. The system may further include a processor that is configured to register the at least one first medical image to the second medical image, determine a classifier model using the registered first medical image and the corresponding first structure label map, and determine a second structure label map associated with the second medical image using the classifier model.

Certain embodiments of the present disclosure relate to a computer-implemented method for segmenting medical images. The method may include the operations performed by at least one processor. The operations may include receiving at least one first medical image of an object, and a second medical image of the object, from a database configured to store a plurality of medical images acquired by an image acquisition device, each first medical image associated with a first structure label map. The operations may further include registering the at least one first medical image to the second medical image, determining a classifier model using the registered first medical image and the corresponding first structure label map, and determining a second structure label map associated with the second medical image using the classifier model.

Certain embodiments of the present disclosure relate to a non-transitory computer-readable medium containing instructions that, when executable by at least one processor, cause the at least one processor to perform a method for segmenting medical images. The method may include receiving at least one first medical image of an object, and a second medical image of the object, from a database configured to store a plurality of medical images acquired by an image acquisition device, each first medical image associated with a first structure label map. The method may further include registering at least one first medical image to the second medical image, determining a classifier model using the registered first medical image and the corresponding first structure label map, and determining a second structure label map associated with the second medical image using the classifier model.

Additional features and advantages of the present disclosure will be set forth in part in the following description, and in part will be obvious from the description, or may be learned by practice of the present disclosure. The features and advantages of the present disclosure will be realized and attained by means of the elements and combinations pointed out in the appended claims.

It is to be understood that the foregoing general description and the following detailed description are exemplary and explanatory only, and are not restrictive of the invention, as claimed.

BRIEF DESCRIPTION OF THE DRAWINGS

The accompanying drawings, which constitute apart of this specification, illustrate several embodiments and, together with the description, serve to explain the disclosed principles.

DETAILED DESCRIPTION

Figure 1:
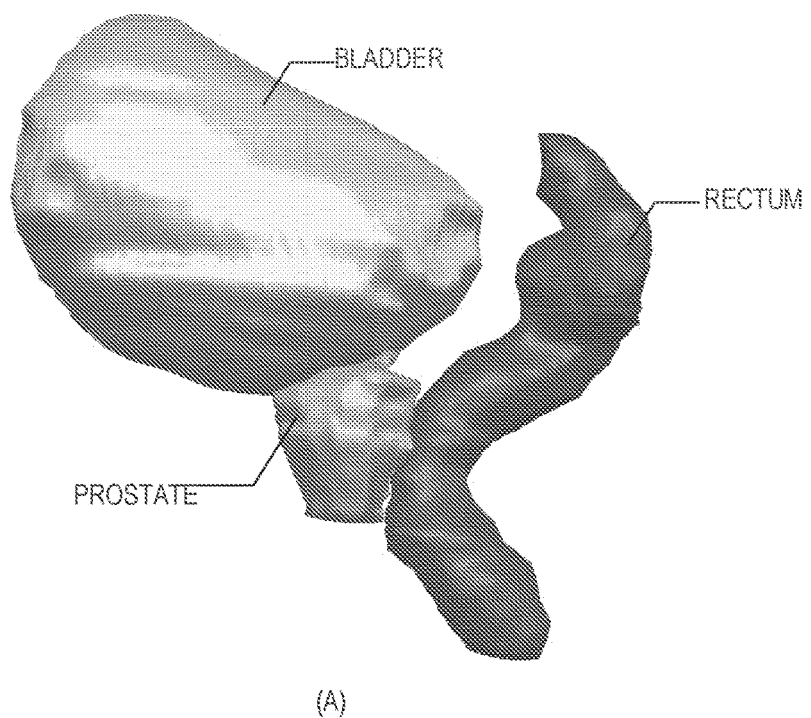
FIG. 1 illustrates an exemplary 3D CT image from a typical prostate cancer patient.
Figure 1:
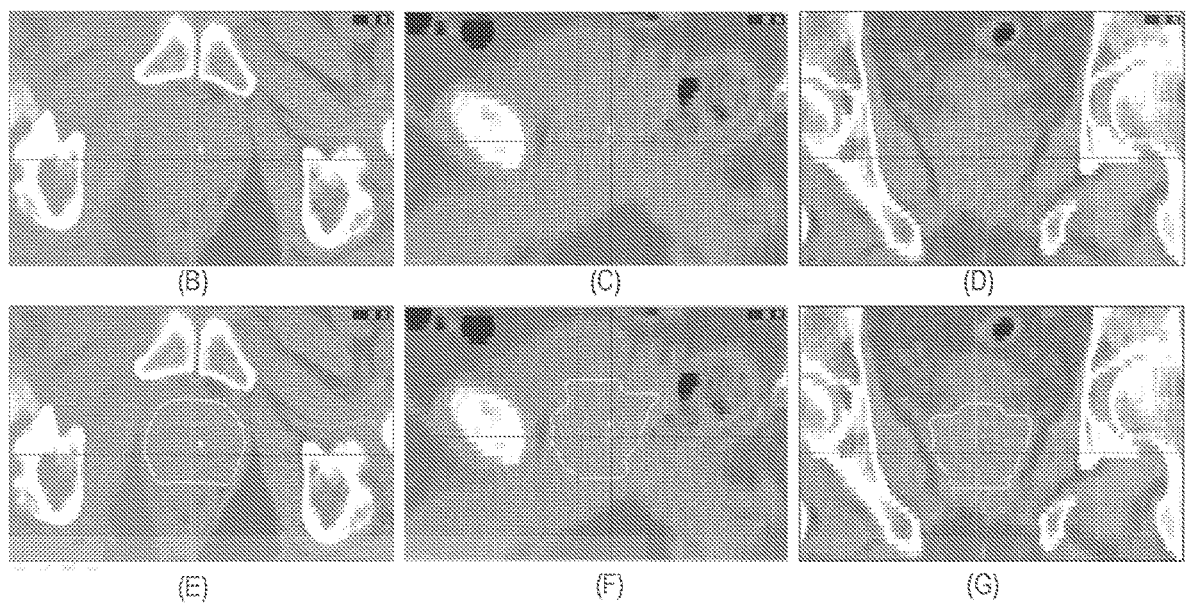

While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be interpreted as open ended, such that an item or items following any one of these words is not meant to be an exhaustive listing of the item or items, or meant to be limited to only the listed item or items. And the singular forms "a," "an," and "the" are intended to include plural references, unless the context clearly dictates otherwise.

Systems and methods consistent with the present disclosure are directed to segmenting a medical image of an object using learning algorithms trained using mapped atlases derived based on prior images of the same object. Specifically, embodiments of the present disclosure provide various combinations of atlas-based auto-segmentation (ABAS) and Random Forest (RF) segmentations of serial CT images, incorporating patient-specific RF models learned on prior-day images and their structures.

As used herein, a "learning algorithm" refers to any algorithm that can learn a model or a pattern based on existing information or knowledge. The learned model or pattern can be then used to predict or estimate output using input of new information or knowledge. For example, the learning algorithm may be a machine learning algorithm or any other suitable learning algorithm. In some embodiments, a supervised learning algorithm, such as a Support Vector Machine (SVM), Adaboost/Logitboost, Random Forests, and neural network (e.g., a convolutional neural network), may be used. In some other embodiments, semi-supervised learning algorithms may also be used.

Supervised learning is a branch of machine learning that infers a prediction model given a set of training data. Each individual sample of the training data is a pair containing a data vector (such as a series of measurements) and a desired output value. A supervised learning algorithm analyzes the training data and produces a predictor function. The predictor function is called a classifier or a classification model when the output is discrete, such as a list of labels identifying different groups. The predictor function, once derived through training, is capable of predicting the correct output value for a valid input.

Consistent with the disclosed embodiments, image segmentation may be formulated as a learning-based classification function, which classifies each image point of the medical image into one of the anatomical structures. As used herein, an "image point" refers to an image element in a digital image that corresponds to a physical point in the underlying object. For example, the image point is a pixel in a 2D image or a voxel in a 3D image.

Consistent with the disclosed embodiments, the image segmentation may also classify image blocks rather than image points. As used herein, an "image block" is a group of image points to be classified together. For example, the image block may be a super-pixel in a 2D image, or a super-voxel in a 3D image. When image points within an image block are known to belong to the same anatomical structure, classifying based on image blocks may be more efficient and accurate. Accordingly, whenever the term "image point" is used throughout this disclosure, it intends to cover both the basic "image point" and also the "image block" as defined above.

The disclosed systems and methods provide an estimated structure label map for the image. A label map refers to a map of structure labels each identifying a corresponding image point as being within a particular structure of interest. Alternatively, consistent with this disclosure, a label map may also be a probability map, which contains structure labels that each represents the probability of the image point belonging to the structure. For example, when segmenting an image including multiple structures, a structure label of an image point may provide a set of probability values indicting how likely the image point belonging to each of the structures under consideration.

Consistent with the disclosed embodiments, the classifier is trained using a set of training images. As used herein, a "training image" is an image where the image points are already classified and labeled. For example, a training image may be an atlas. As used consistently herein, an "atlas" includes an image and corresponding structure delineations (annotations) indicating what structure(s) the image points belong to. The image in an atlas, also referred to as an atlas image, can be a previous image of the subject patient taken at an earlier time. The structure delineations can be represented as, for example, structure label maps, structure surfaces, or structure contours. The description below uses the label maps as an example of the structure delineations and is similarly applied to the scenarios of structure surfaces and contours.

Consistent with the disclosed embodiments, the training process uses features extracted from the atlas image and the corresponding structure delineations to train a classifier. Once properly trained using the process discussed in more detail below, such an algorithm can be used to segment a new image.

Consistent with the disclosed embodiments, the atlases used in the training process may be derived from prior images of the same object as the new image to be segmented. Similarity between such training images and the new image to be segmented can improve the segmentation accuracy and efficiency. In some embodiments, the atlases used to train a classifier may be obtained by segmenting a previous image using a previously trained classifier. In some embodiments, the atlases used may be registered to the current image.

Consistent with the disclosed embodiments, intra-patient images obtained during the course of radiation therapy are used. The intra-patient images are typically obtained one or more days between images to check on the patient's response to the prescribed therapy. Delineating the anatomy of serial images of the same patient's anatomy using the patient's prior-image information aids in the segmentation of succeeding images. Accurate serial image segmentation is a prerequisite for adaptive therapy plan assessment/re-planning and dose accumulation.

Consistent with the disclosed embodiments, the combination of Atlas-based auto-segmentation (ABAS) and statistical learning (SL) segmentations of serial CT images may improve segmented serial images of the same patient during adaptive planning and determining dose accumulation. This combination may also improve the prediction accuracy and thus the quality of image segmentation. In addition, the use of prior days' images and structures deformably registered to succeeding days' images to form statistical models may provide more accurate segmentations than models based on unregistered images.

Atlas-based segmentation registers an image with anatomy labels attached to its voxels (the atlas) to a target image, and then assigns the atlas labels to the corresponding target voxels. Statistical learning assigns target voxel labels using a classifier program in which labels are associated with regions of a feature space. The features include voxel intensity, appearance (local variation measures), and structural properties of the images. The label-feature association is learned by training the classifier program on labeled images.

In an embodiment, the statistical learning method used is the Random Forests (RF) method. A random forest is a set of decision trees. Starting with a random sample of the training data (such as voxel average intensities for voxel patches, and pairs of patches located randomly around the index voxel), and a random selection of variables embedded in the data, the method determines the best parameter split of the samples into the label categories, splits the data sample, and then follows the split data down to the next pair of nodes where the best split is found. In an embodiment, this method is recursively performed until terminating at the maximum tree depth, or until a minimum sample size is reached. The terminal tree nodes (e.g., leaves) provide a label assignment. Trees thus trained perform classification when new feature data is processed through the trees' nodes. Multiple trees increase the discriminative power of the classifier. Random forest classifiers resist overfitting, and can be used for efficient image segmentations. Segmentation methods incorporating patient-specific RF models learned on prior-day images and their structures provide more accurate segmentation than methods than methods that solely use a population model.

Although the combination of ABAS and RF segmentations is used as an exemplary combination consistent with the present disclosed, other statistical learning algorithms and various combinations with ABAS are contemplated, including those learning algorithms discussed above. Further, the disclosed image segmentation systems and methods can be applied to segment medical images obtained from any type of imaging modalities, including, but not limited to X-ray, CT, CBCT, spiral CT, magnetic resonance imaging (MRI), ultrasound (US), positron emission tomography (PET), single-photon emission computed tomography (SPECT), and optical images. Furthermore, the disclosed image segmentation systems and methods can be adapted to segment both 2D and 3D images.

Exemplary embodiments are now described with reference to the accompanying drawings. Wherever convenient, the same reference numbers are used throughout the drawings to refer to the same or like parts.

Figure 2A:
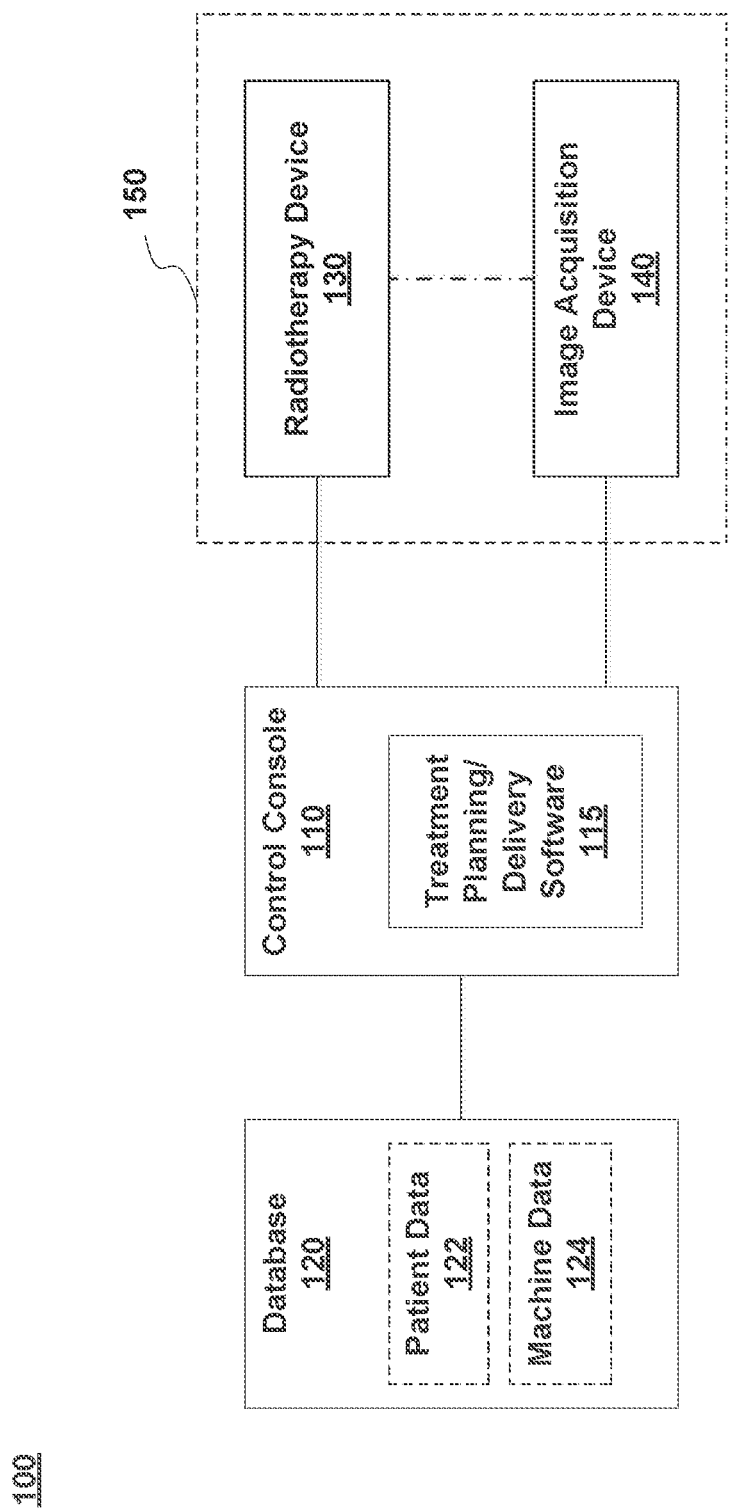
FIG. 2A is a block diagram showing an exemplary radiotherapy system 100, according to some embodiments of the present disclosure.

FIG. 2A is a block diagram showing an exemplary radiotherapy system 100, according to some embodiments of the present disclosure. Radiotherapy system 100 may be an IGRT system. As shown in FIG. 2A, radiotherapy system 100 may include a control console 110, a database 120, a radiotherapy device 130, and an image acquisition device 140. In some embodiments, radiotherapy device 130 and image acquisition device 140 may be integrated into a single image-guided radiotherapy device 150, as indicated by the dashed box 150 in FIG. 2A. In some embodiments, radiotherapy device 130 and image acquisition device 140 may be separate devices. In some embodiments, radiotherapy device 130 and image acquisition device 140 may be physically or communicative connected to each other, as indicated by a dotted-dashed line between radiotherapy device 130 and image acquisition device 140 in FIG. 2A.

Control console 110 may include hardware and software components to control radiotherapy device 130 and image acquisition device 140 and/or to perform functions or operations such as treatment planning, treatment execution, image acquisition, image processing, motion tracking, motion management, or other tasks involved in a radiotherapy process. The hardware components of control console 110 may include one or more computers (e.g., general purpose computers, workstations, servers, terminals, portable/mobile devices, etc.), processor devices (e.g., central processing units (CPUs), graphics processing units (GPUs), microprocessors, digital signal processors (DSPs), field programmable gate arrays (FPGAs), special-purpose or specially-designed processors, etc.); memory/storage devices (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); or other suitable hardware. The software components of control console 110 may include operation system software, application software, etc. For example, as shown in FIG. 2A, control console 110 may include treatment planning/delivery software 115 that may be stored in a memory/storage device of control console 110. Software 115 may include computer readable and executable codes or instructions for performing the processes described in detail below. For example, a processor device of control console 110 may be communicatively connected to a memory/storage device storing software 115 to access and execute the codes or instructions. The execution of the codes or instructions may cause the processor device to perform operations to achieve one or more functions consistent with the disclosed embodiments.

Control console 110 may be communicatively connected to database 120 to access data. In some embodiments, database 120 may be implemented using local hardware devices, such as one or more hard drives, optical disks, and/or servers that are in the proximity of control console 110. In some embodiments, database 120 may be implemented in a data center or a server located remotely with respect to control console 110. Control console 110 may access data stored in database 120 through wired or wireless communication.

Database 120 may include patient data 122. Patient data may include information such as (1) imaging data associated with a patient anatomical region, organ, or volume of interest segmentation data (e.g., MRI, CT, X-ray, PET, SPECT, and the like); (2) functional organ modeling data (e.g., serial versus parallel organs, and appropriate dose response models); (3) radiation dosage data (e.g., may include dose-volume histogram (DVH) information); or (4) other clinical information about the patient or course of treatment.

Database 120 may include machine data 124. Machine data 124 may include information associated with radiotherapy device 130, image acquisition device 140, or other machines relevant to radiotherapy, such as radiation beam size, arc placement, on/off time duration, radiation treatment plan data, multi-leaf collimator (MLC) configuration, MRI pulse sequence, and the like.

Image acquisition device 140 may provide medical images of a patient. For example, image acquisition device 140 may provide one or more of MRI images (e.g., 2D MRI, 3D MRI, 2D streaming MRI, 4D volumetric MRI, 4D cine MRI); Computed Tomography (CT) images; Cone-Beam CT images; Positron Emission Tomography (PET) images; functional MRI images (e.g., fMRI, DCE-MRI, diffusion MRI); X-ray images; fluoroscopic images; ultrasound images; radiotherapy portal images; Single-Photo Emission Computed Tomography (SPECT) images; and the like. Accordingly, image acquisition device 140 may include an MRI imaging device, a CT imaging device, a PET imaging device, an ultrasound imaging device, a fluoroscopic device, a SPECT imaging device, or other medical imaging devices for obtaining the medical images of the patient.

Radiotherapy device 130 may include a Leksell Gamma Knife, a linear accelerator or LINAC, or other suitable devices capable of delivering radiation to an anatomical region of interest of a patient in a controllable manner.

Figure 2B:
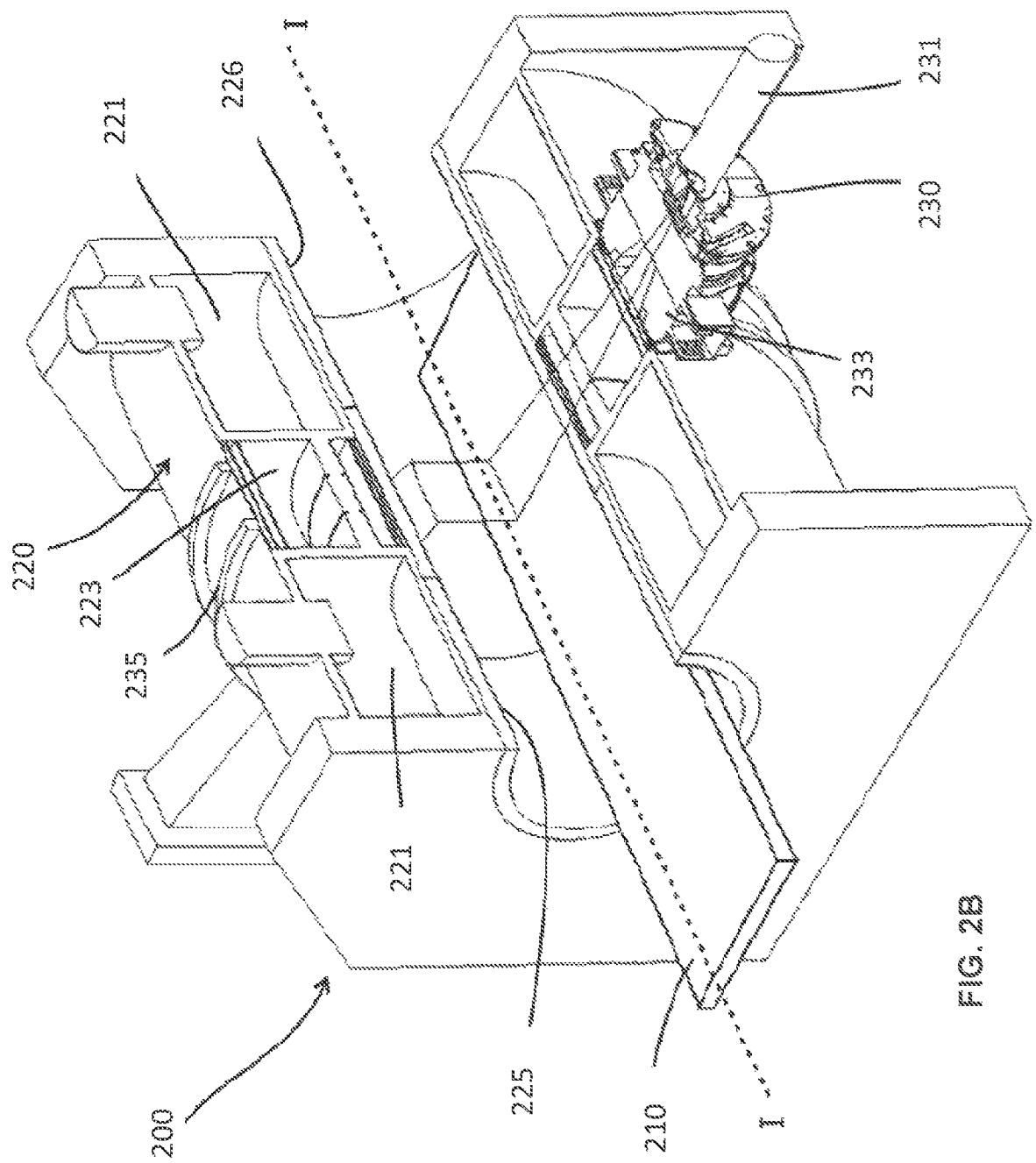
FIG. 2B depicts an exemplary image-guided radiotherapy device, according to some embodiments of the present disclosure.

FIG. 2B depicts an exemplary image-guided radiotherapy system 200, consistent with disclosed embodiments. Consistent with some embodiments, the disclosed image segmentation system may be part of a radiotherapy system as described with reference to FIG. 2A. As shown, system 200 may include a couch 210, an image acquisition device 220, and a radiation delivery device 230. System 200 delivers radiation therapy to a patient in accordance with a radiotherapy treatment plan.

Couch 210 may support a patient (not shown) during a treatment session. In some implementations, couch 210 may move along a horizontal, translation axis (labelled "I"), such that couch 210 can move the patient resting on couch 210 into and/or out of system 200. Couch 210 may also rotate around a central vertical axis of rotation, transverse to the translation axis. To allow such movement or rotation, couch 210 may have motors (not shown) enabling the couch to move in various directions and to rotate along various axes. A controller (not shown) may control these movements or rotations in order to properly position the patient according to a treatment plan.

In some embodiments, image acquisition device 220 may include an MRI machine used to acquire 2D or 3D MRI images of the patient before, during, and/or after a treatment session. Image acquisition device 220 may include a magnet 221 for generating a primary magnetic field for magnetic resonance imaging. The magnetic field lines generated by operation of magnet 221 may run substantially parallel to the central translation axis. Magnet 221 may include one or more coils with an axis that runs parallel to the translation axis I. In some embodiments, the one or more coils in magnet 221 may be spaced such that a central window 223 of magnet 221 is free of coils. In other embodiments, the coils in magnet 221 may be thin enough or of a reduced density such that they are substantially transparent to radiation of the wavelength generated by radiotherapy device 230. Image acquisition device 220 may also include one or more shielding coils, which may generate a magnetic field outside magnet 221 of approximately equal magnitude and opposite polarity in order to cancel or reduce any magnetic field outside of magnet 221. As described below, radiation source 231 of radiotherapy device 230 may be positioned in the region where the magnetic field is cancelled, at least to a first order, or reduced.

Image acquisition device 220 may also include two gradient coils 225 and 226, which may generate a gradient magnetic field that is superposed on the primary magnetic field. Coils 225 and 226 may generate a gradient in the resultant magnetic field that allows spatial encoding of the protons so that their position can be determined. Gradient coils 225 and 226 may be positioned around a common central axis with the magnet 221, and may be displaced along that central axis. The displacement may create a gap, or window, between coils 225 and 226. In the embodiments wherein magnet 221 also includes a central window 223 between coils, the two windows may be aligned with each other. In some embodiments, image acquisition device 220 may be an imaging device other than an MRI, such as an X-ray, a CT, a CBCT, a spiral CT, a PET, a SPECT, an optical tomography, a fluorescence imaging, ultrasound imaging, or radiotherapy portal imaging device.

Radiotherapy device 230 may include the source of radiation 231, such as an X-ray source or a linear accelerator, and a multi-leaf collimator (MLC) 233. Radiotherapy device 230 may be mounted on a chassis 235. One or more chassis motors (not shown) may rotate chassis 235 around couch 210 when couch 210 is inserted into the treatment area. In an embodiment, chassis 235 may be continuously rotatable around couch 210, when couch 210 is inserted into the treatment area. Chassis 235 may also have an attached radiation detector (not shown), preferably located opposite to radiation source 231 and with the rotational axis of chassis 335 positioned between radiation source 231 and the detector. Further, device 230 may include control circuitry (not shown) used to control, for example, one or more of couch 210, image acquisition device 220, and radiotherapy device 230. The control circuitry of radiotherapy device 230 may be integrated within system 200 or remote from it.

During a radiotherapy treatment session, a patient may be positioned on couch 210. System 200 may then move couch 310 into the treatment area defined by magnetic coils 221, 225, 226, and chassis 235. Control console 240 may then control radiation source 231, MLC 233, and the chassis motor(s) to deliver radiation to the patient through the window between coils 225 and 226 according to a radiotherapy treatment plan.

Figure 3:
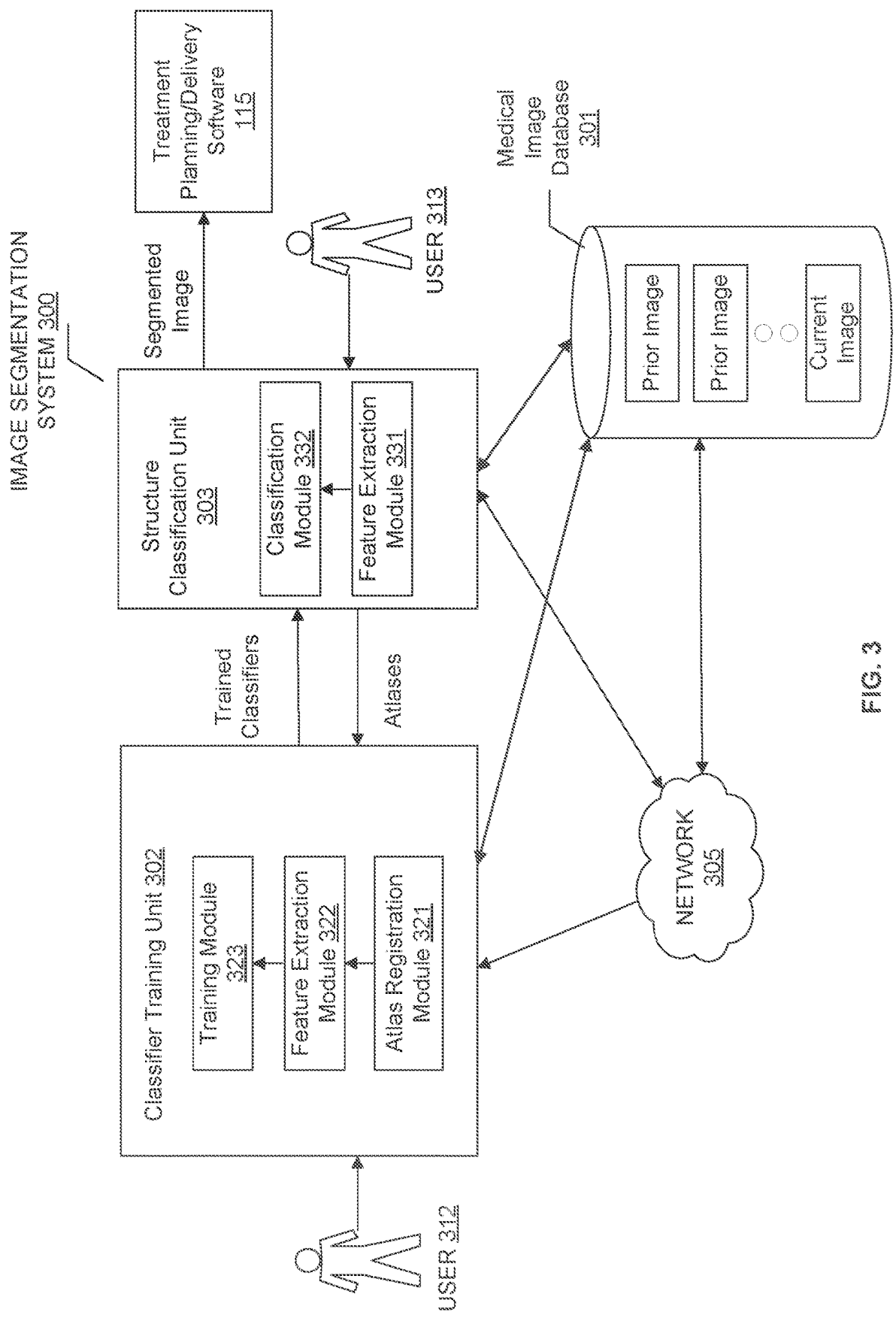
FIG. 3 illustrates an exemplary image segmentation system, according to some embodiments of the present disclosure.

FIG. 3 illustrates an exemplary image segmentation system 300 for segmenting medical images, according to some embodiments of the present disclosure. Image segmentation system 300 may include a medical image database 301, a classifier training unit 302, a structure classification unit 303, and a network 305. In some embodiments, image segmentation system 300 may include more or less of the components shown in FIG. 3. For example, when an anatomical classifier is pre-trained and provided, image segmentation system 300 may only include structure classification unit 303, medical image database 301, and, optionally, network 305.

In some embodiments, the various components of image segmentation system 300 may locate remotely from each other, and be connected through network 305. In some alternative embodiments, certain components of image segmentation system 300 may be located on the same site or inside one device. For example, medical image database 301 may be located on site with classifier training unit 302, or be part of classifier training unit 302. As another example, classifier training unit 302 and structure classification unit 303 may be inside the same computer or processing device.

Image segmentation system 300 may be used to segment serial intra-patient CT images stored in medical image database 301. Consistent with the disclosure, "serial images" may be images acquired during serial radiotherapy treatment sessions of a patient. The serial radiotherapy treatment sessions may be performed at a set frequency (e.g., every day, every week, etc.) or at discrete time points, according to a radiotherapy treatment plan for the patient. The serial images may include current images and prior images. In some embodiments, a "current image" may be a current day medical image of a patient, e.g., an image taken during the treatment session of a patient that occurred on the present day. As shown in FIG. 3, classifier training unit 302 may communicate with medical image database 301 to receive one or more "prior images" of the same patient. A "prior image" may be an image taken during a treatment session of the same patient but occurred on a previous day. The prior images stored in medical image database 301 may be obtained from a medical image database, which contain images of previous radiotherapy treatment sessions.

In some embodiments, the prior images may be pre-segmented. For example, the prior images may be segmented automatically by image segmentation system 300, or manually by user 313. User 313 may be an expert, e.g., a radiologist or another physician familiar with anatomical structures in medical images, who provides expert structure label maps associated with the prior images. In that case, the prior images and their corresponding structure label maps become atlases that can be readily used by classifier training unit 302 to train a structure classifier.

If the prior images are not pre-segmented, they may be sent to structure classification unit 303 for segmentation. In some embodiments, structure classification unit 303 may use the most recently trained classifier to segment the prior images, or a merged classifier of selected previously trained classifiers for the segmentation. Structure classification unit 303 may provide a structure label map for each prior image. Structure classification unit 303 may then provide the atlases, consisting of the prior images along with their corresponding structure label maps, to classifier training unit 302, as training images.

Classifier training unit 302 may use the training images received from medical image database 301 to generate a structure classifier using learning algorithms. As shown in FIG. 3, classifier training unit 302 may include an atlas registration module 321, a feature extraction module 322 and a training module 323. Classifier training unit 302 may additionally include input and output interfaces (not shown) to communicate with medical image database 301, network 305, and/or user 312. Consistent with some embodiments, classifier training unit 302 may be implemented with hardware (e.g., as disclosed in FIG. 4) specially programmed by software that performs an anatomical classifier training process.

Atlas registration module 321 may register the prior images to the current images. Image registration is a process that transforms different sets of data into one coordinate system. Typical image registration algorithms are either intensity-based or feature-based, or the combination of the two. In particular, feature-based methods find correspondence between image features such as points, lines, and contours. In some embodiments, the registration process may include mapping the image points of an atlas image to the image points of a current image. In some alternative embodiments, the registration process may include mapping both the atlas images and the current image to a reference image. In these embodiments, the reference image can be, for example, an average atlas image or a common template image. As such, the atlas images are "indirectly" mapped to the current image. Various image registration methods can be used, such as one or a combination of any of a linear registration, an object-driven "poly-smooth" non-linear registration, or a shape-constrained dense deformable registration. By performing the image registration, an image transformation from the atlas image to the reference image is calculated for each atlas.

Atlas registration module 321 may further map the delineations (e.g., structure labels) of each atlas to the space of the reference image using the corresponding image transformation for the atlas. The mapped structure labels represent independent classification data, i.e., independent segmentation results, of the current image from the corresponding atlas.

A mapped atlas image and corresponding mapped structure labels constitute a mapped atlas, also referred to as a "registered atlas." In some embodiments, classifier training unit 302 may use the mapped atlases to train the structure classifier for segmenting the current images. Alternatively, classifier training unit 302 may use the mapped atlas images along with expert structure label maps for the training.

Feature extraction module 322 may determine and derive, for each selected image point, one or more features such as image intensity, image texture, image patch, and curvature of an intensity profile. This feature extraction process may repeat for a set of selected image points in a training image until all image points in the training image have been selected and processed.

Training module 323 may use the selected image points as training data, to train the classifier. In some embodiments, the training may be based on learning algorithms, such as supervised machine learning algorithms. For example, learning algorithms such as Support Vector Machine (SVM), Adaboost/Logitboost, Random Forests, and Neural Networks may be used. The classifier is trained such that when the features for a particular image point in the training image are input to the model, the model outputs a prediction of the anatomical structure that matches the predetermined structure label of the image point. After being trained using numerous image points from numerous training images, the classifier becomes competent enough to predict the anatomical structure of an unclassified image point in any new image.

Structure classification unit 303 may receive the trained structure classifier from classifier training unit 302. As shown in FIG. 3, structure classification unit 303 may include a feature extraction module 331 and a classification module 332. Structure classification unit 303 may additionally include input and output interfaces (not shown) to communicate with medical image database 301, network 305 and user 313. Consistent with some embodiments, structure classification unit 303 may be implemented with hardware (e.g., as disclosed in FIG. 4) specially programmed by software that performs an anatomical classifier training process.

Structure classification unit 303 may communicate with medical image database 301 to receive one or more current images. The current images may be of a same object as the prior images. Feature extraction module 331 may have similar hardware and software structures as feature extraction module 322. Feature extraction module 331 may identify one or more features on each current image received from medical image database 301. The features extracted by feature extraction module 331 may be the same or similar to those used during the training stage by feature extraction module 322. The determined features may be provided to classification module 332.

Classification module 332 may use the trained structure classifier received from classifier training unit 302, and the features received from feature extraction module 331, to predict the structure labels for the respective image points. When all the selected image points are classified, classification module 332 may output the segmented image. In some embodiments, the segmented image may be displayed to user 313, and/or provided to treatment planning/delivery software 115 for further treatment usage. In some embodiments, the segmented image may be automatically stored in medical image database 301 and become a prior image.

Network 305 may provide connections between any of the above described components in image segmentation system 300. For example, network 305 may be a local area network (LAN), a wireless network, a cloud computing environment (e.g., software as a service, platform as a service, infrastructure as a service), a client-server, a wide area network (WAN), and the like.

Figure 4:
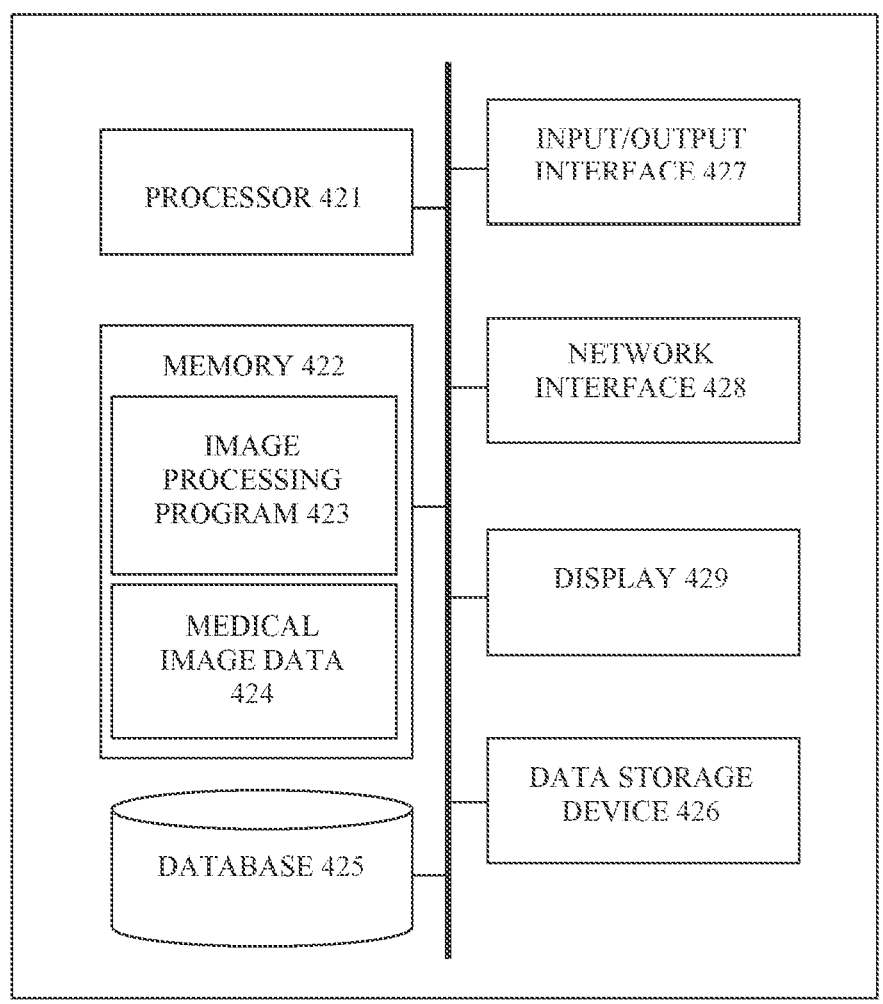
FIG. 4 illustrates an exemplary medical image processing device, according to some embodiments of the present disclosure.

FIG. 4 illustrates an exemplary medical image processing device 400, according to some embodiments of the present disclosure. Medical image processing device 400 may be an embodiment of classifier training unit 302, structure classification unit 303, or their combination. In another embodiment, processing device 400 may be integrated into control console 110 or radiotherapy device 230, shown in FIGS. 2A-(B). In some embodiments, medical image processing device 400 may be a special-purpose computer, or a general-purpose computer. For example, medical image processing device 400 may be a computer custom built for hospitals to handle image acquisition and image processing tasks.

As shown in FIG. 4, medical image processing device 400 may include a processor 421, a memory 422, a database 425, a data storage device 426, an input/output interface 427, a network interface 428, and a display 429. Components of processing device 400 may be connected via a BUS.

Processor 421 may be one or more general-purpose processing devices, such as a microprocessor, central processing unit (CPU), graphics processing unit (GPU), or the like. More particularly, processor 421 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Processor 421 may also be one or more special-purpose processing devices such as an application specific integrated circuit (ASIC), a field programmable gate array (FPGA), a digital signal processor (DSP), a System on a Chip (SoC), or the like. Processor 421 may be communicatively coupled to memory 422 and configured to execute the computer executable instructions stored thereon.

Memory 422 may include a read-only memory (ROM), a flash memory, a random access memory (RAM), and a static memory, for example. In some embodiments, memory 422 may store computer executable instructions, such as one or more image processing programs 423, as well as data used or generated while executing the computer programs, such as medical image data 424. Processor 421 may execute image processing programs 423 to implement functionalities of anatomical classifier training unit 302 and/or structure classification unit 303. Processor 421 may also send/receive medical image data 424 from memory 422. For example, processor 421 may receive prior image data or current image data stored in memory 422. Processor 421 may also generate intermediate data such as image features and structure labels, and send them to memory 422.

Medical image processing device 400 may optionally include a database 425, which may include or in communication with medical image database 301. Database 425 may include a plurality of devices located either in a central or distributed manner. Processor 421 may communicate with database 425 to read images into memory 422 or store segmented images from memory 422 to medical image data 424.

Data storage device 426 may be an additional storage available to store data associated with image processing tasks performed by processor 421. In some embodiments, data storage device 426 may include a machine-readable storage medium. While the machine-readable storage medium in an embodiment may be a single medium, the term "machine-readable storage medium" should be taken to include a single medium or multiple media (e.g., a centralized or distributed database, and/or associated caches and servers) that store the one or more sets of computer executable instructions or data. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical and magnetic media.

Input/output 427 may be configured to allow data to be received and/or transmitted by medical image processing device 400. Input/output 427 may include one or more digital and/or analog communication devices that allow processing device 400 to communicate with user or other machines and devices. For example, input/output 427 may include a keyboard and a mouse for user 312 or user 313 to provide input.

Network interface 428 may include a network adaptor, a cable connector, a serial connector, a USB connector, a parallel connector, a high-speed data transmission adaptor such as fiber, USB 3.0, thunderbolt, and the like, a wireless network adaptor such as a WiFi adaptor, a telecommunication (3G, 4G/LTE and the like) adaptor, and the like. Medical image processing device 400 may be connected to network 305 through network interface 428. Display 429 may be any display device that suitable for displaying the medical images. For example, display 429 may be an LCD, CRT, or LED display.

In some embodiments, the segmented current image may be displayed to a user on display 428. In some embodiments, the segmented current image may be provided to treatment planning/delivery software 115 for future medical usage and/or stored in medical image database 301 for future image segmentation tasks.

An accurately segmented image, or a well-defined contour of an anatomical structure may benefit various applications that rely on segmentation results. For example, structure classification results may also help generate accurate estimation of volume size of the anatomical structure.

For certain anatomical structures, such as the bladder, volume sizes are important in calculating the deformation field and dose optimization for treatments. In the example of bladder, the volume sizes may change significantly at different treatment sessions. Therefore, accurate estimation of its size will give important prior knowledge about the relative locations or deformations around the bladder, and thus help calculate the deformation field or optimize dose distribution on the fly.

Figure 5:
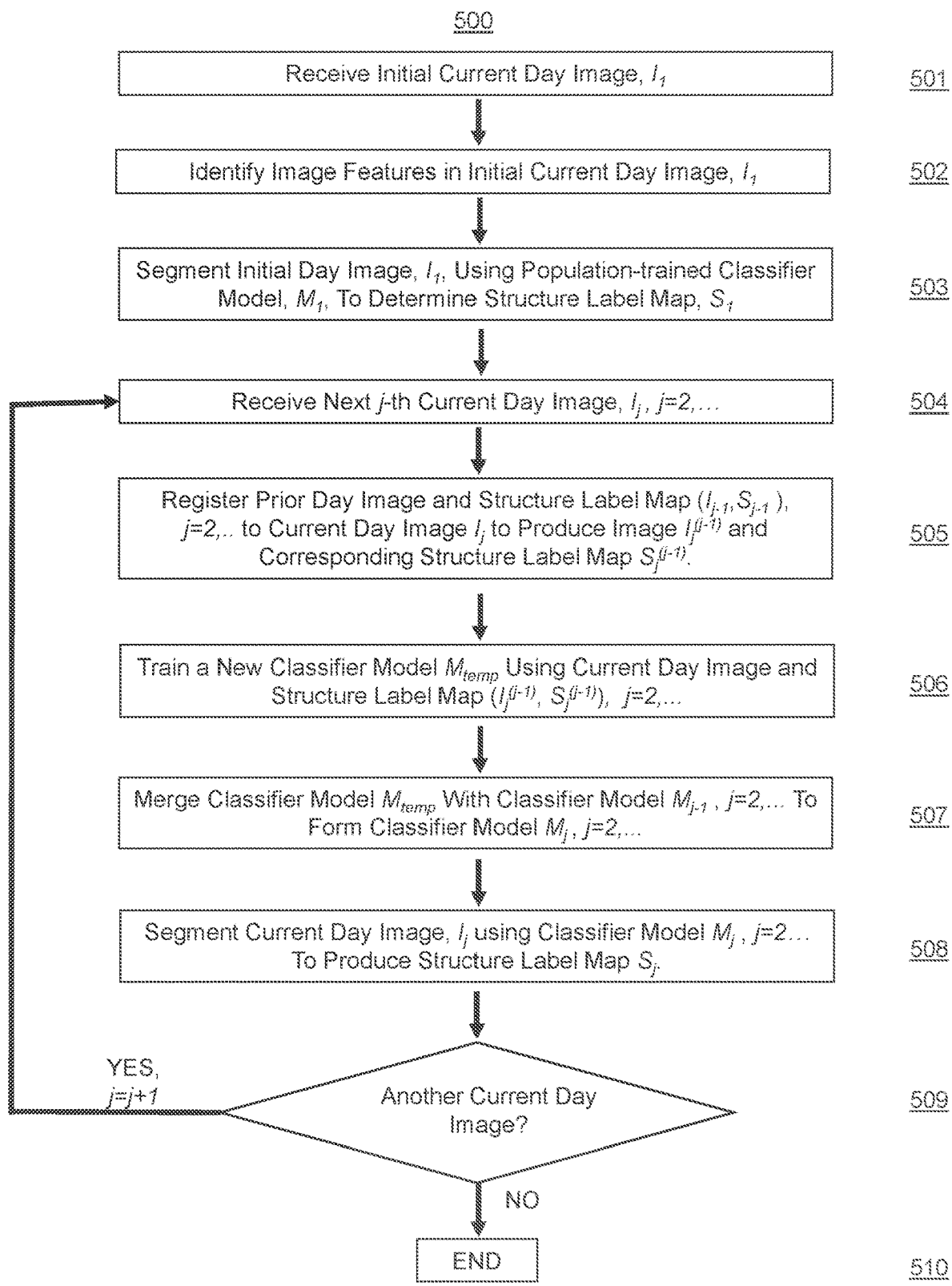
FIG. 5 is a flowchart illustrating an exemplary image segmentation process, according to some embodiments of the present disclosure.

FIG. 5 is a flowchart illustrating an exemplary image segmentation method 500 using combined atlas-based segmentation and statistical learning segmentation. In some embodiments, method 500 may be performed by components of image segmentation system 300, such as classifier training unit 302 and structure classification unit 303. It is contemplated that method 500 can be applied to segment one structure of interest or a group of structures of interest at the same time, such as a bladder, prostate, and rectum, which are spatially adjacent and highly correlated. Various machine learning methods, such as RF method, can handle segmentation of multiple structures at the same time. A multi-structure classifier model may be beneficial when the multiple structures are spatially adjacent and thus highly correlated.

As shown in FIG. 5, at 501, medical image processing device 400 may receive an initial day medical image $I_1$ from a database, such as medical image database 301. In some embodiments, medical image $I_1$ represents a prior day medical image of a patient at day one.

At 502, medical image processing device 400 may identify at least one feature from the day one image $I_1$. The at least one feature may be identified by feature extraction module 332 of structure classification unit 303, for example. The features can be the same types of features used for training the structure classifier, as will be described in more detail below in connection with FIG. 6. Various methods may be used to compute the attributes, including using machine learning models such as convolutional neural network models.

At 503, the day one image $I_1$ is segmented by a population-trained classifier model $M_1$. For example, the day one image may be segmented by a random forests model $M_1$ trained on training images from a population of patients. The day one image $I_1$ may be segmented by the population-trained $M_1$ to produce a structure label map $S_1$, e.g., representing the prostate, bladder, rectum, and/or other organs.

At 504, medical image processing device 400 may receive the j-th succeeding day medical image $I_1$ from a database, such as medical image database 301. Medical image $I_j$ represents a succeeding day medical image of the same patient at day two, or any succeeding j-th day where j=2, . . . . In some embodiments, day one image $I_1$ and succeeding day medical image $I_j$ are acquired during serial radiotherapy treatment sessions of the same patient. For example, the medical images may be acquired by image acquisition device 220 during successive treatment therapy sessions delivered by image-guided radiotherapy system 200.

At 505, the prior day image $I_{j-1}$, j=2, . . . and its corresponding structure label map $S_{j-1}$ from step 603 may be used as an atlas and registered to the current day image $I_j$ to obtain a registered image $I_j^{(j-1)}$ and a corresponding atlas-based segmentation structure label map $S_j^{(j-1)}$. For example, $I_1$, $S_1$ is used as an atlas to deformably register $I_1$ to day two image $I_2$ to obtain the registered image $I_2^{(1)}$ and day two structure label map $S_2^{(1)}$. The superscript refers to the atlas-day number, and serves to distinguish the preliminary segmentation result $S_j^{(j-1)}$ from the full-model classification $S_j$ described below in 508.

At 506, a classifier model $M_{temp}$ is trained on the image $I_j^{(j-1)}$ and the structure map $S_j^{(j-1)}$ obtained as described above in step 505. In some embodiments, the model may be trained according to an exemplary training method described in FIG. 6. For example, a new random forest model $M_{temp}$ may be trained on the set $I_j^{(j-1)}$, $S_j^{(j-1)}$.

At 507, the trained new classifier model $M_{temp}$ is merged with the prior day classifier model $M_{j-1}$ to obtain a new classifier model $M_j$. Various methods may be used to merge the models. For example, the model parameters may be determined based on the model parameters of model $M_{temp}$ and model $M_j$.

At 508, the combined model is used to segment the current day image $I_j$, to produce the structure label map $S_j$. This Structure label map $S_j$ is derived from the model M while the structure label map $S_j^{(j-1)}$ is obtained by atlas-based segmentation using the preceding day data $I_{j-1}$, $S_{j-1}$. As part of 508, feature extractions may be performed on the j-th prior day image, similar to 502.

At 509, the method determines whether all succeeding prior day images for that patient have been used for training the classifier model. If there are more succeeding prior day images for that patient, medical image processing device 400 repeats steps 504-509 to train model $M_j$ (where j represents the j-th treatment day) until all the succeeding prior day images are processed. At 510, the segmentation of current image day $I_j$ is complete.

The model for any j-th treatment day, $M_j$, is obtained by training the classifier on data that is the union of the registered prior day images and their corresponding structure label maps $I_i^{(i-1)}$, $S_j^{(j-1)}$, denoted by $$\left\{ \bigcup_{i=2}^{j} (I_i^{(i-1)}, S_i^{(i-1)}) \right\}, j \geq 2, j = \text{current day}.$$

The training is done in stages, one prior day per stage, resulting in a model $M_{temp}$ that is then combined with prior day's models, as the statistical learning method permits.

In other embodiments the training data ensemble could contain other forms of the structure label maps than that derived from the atlas-based segmentation.

For example, the structure label map could be atlas-based segmentation structures corrected by expert programs or by human experts.

In other embodiments, the population based model $M_1$ (here included in the resulting model $M_j$) could be dissociated from the models $M_2$ to $M_j$.

In other embodiments, the composition of the training data could be varied such that the training data for each j-th treatment day is accumulated from the beginning of treatment and a model created from all the accumulated training data, rather than sequential merging successive days' trained models. This accommodates statistical learning methods such as neural networks that, unlike random or decision forests, have models that are not easily decomposed into daily data-trained increments.

In some embodiments, method 500 may be performed prior to radiotherapy treatment delivery to a patient, and the determined structure label map $S_j$ may be provided to treatment planning/delivery software 115. This segmentation result may be used to adjust the radiotherapy treatment plan. For that purpose, the segmentation (method 500) may be performed immediately prior to the upcoming radiotherapy treatment session, or one day prior to the upcoming radiotherapy treatment session.

Figure 6:
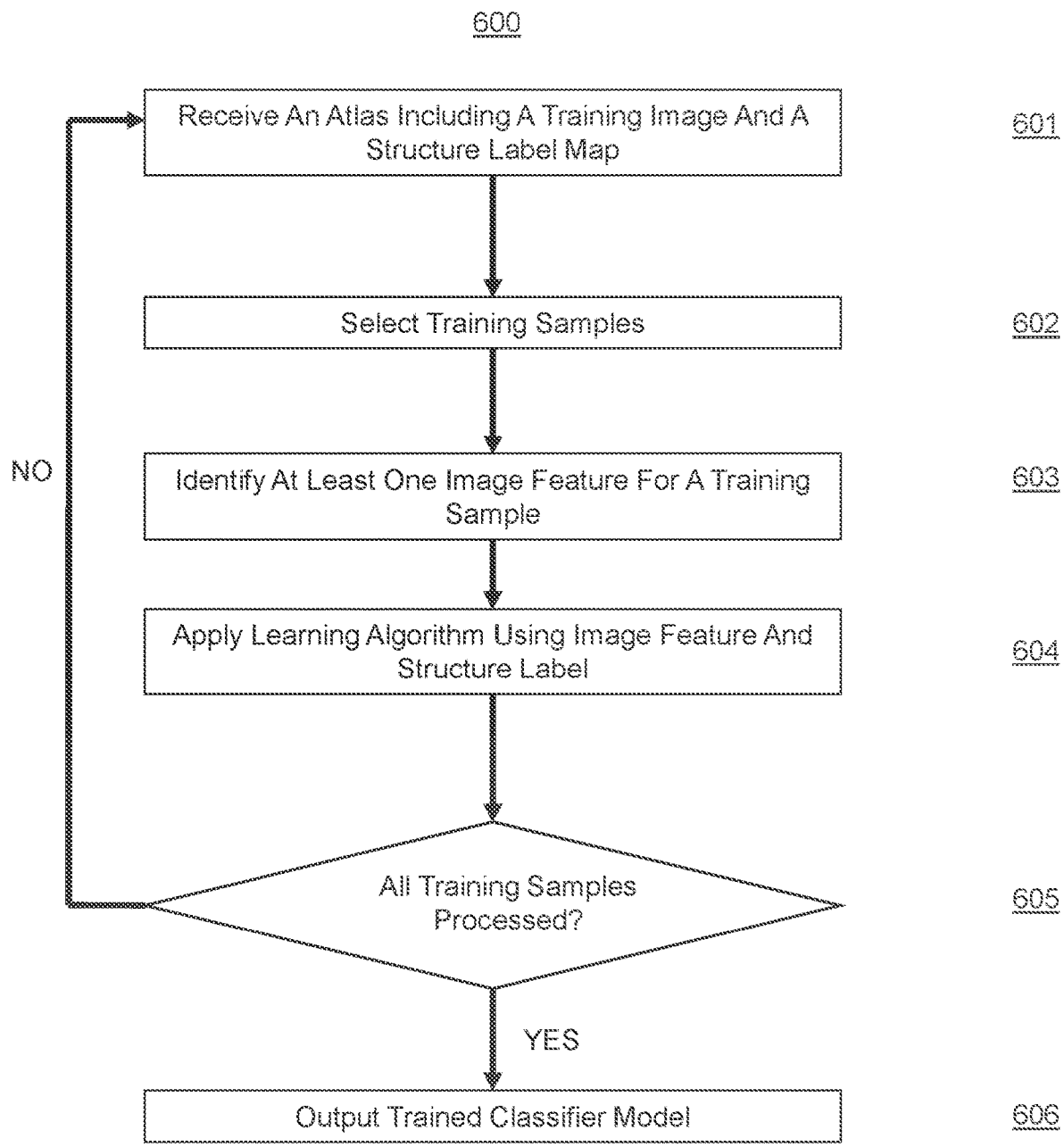
FIG. 6 is a flowchart illustrating an exemplary training method, according to some embodiments of the present disclosure.

FIG. 6 is a flowchart illustrating an exemplary training method 600 for training a structure classifier model using an atlas. In some embodiments, method 600 may be used to implement step 506 of FIG. 5 described above. In some embodiments, method 600 may be performed by classifier training unit 302. The structure classifier model may be a Random Forests model, such as the classifier model $M_j$ of FIG. 5.

As shown in FIG. 6, at 601, classifier training unit 302 may receive an atlas that includes a training image and a corresponding structure label map indicating the structures that the image points of the training image belong to. In some embodiments, the atlas may be a registered atlas, such as atlas $I_j^{(j-1)}$, $S_j^{(j-1)}$.

At 602, feature extraction module 322 may select a plurality of training samples from the mapped atlas image of each training atlas. Each training sample can correspond to a single image point or a group of image points (such a group of image points is also referred to as a super image point). According to the disclosure, the training samples from a mapped atlas image can include all or a portion of the image points on the mapped atlas image. When only a portion of the image points are used for training, a sample selection can be performed to determine what image points are used. For example, the training samples can be selected fully randomly over the entire mapped atlas image, or be selected from a region within a certain distance to the border of the structure of interest. As another example, the sample selection can be guided by the registration results such that more samples can be selected from an ambiguous region, i.e., the region where structure labels from different mapped atlases do not completely agree with each other or the disagreement is larger than a certain level (for example, three or more out of ten mapped atlases have a different determination than the other mapped atlases).

At 603, feature extraction module 322 may determine at least one image feature for an image point. Various types of features can be extracted, such as, for example, image intensity value, image location, image gradient and gradient magnitude, eigen-values of a Hessian matrix of the image, image texture measures such as energy, entropy, contrast, homogeneity, and correlation of local co-occurrence matrix, local image patches of varying sizes. Alternatively, attributes or features may also be automatically and adaptively computed using machine learning models. For example, a convolutional neural network model may be trained to extract relevant features from sample images, and the pre-trained model can be applied to the training samples to produce attributes. A convolutional neural network typically includes several convolution layers, among other layers, that produce feature maps of various sizes. The feature maps contain generic features characterizing the input image (or a selected portion of the input image), and thus can be used as features in the structure classifier to further improve classification results. Features from various convolution layers (e.g., top layers, middle layers, lower layers), or a selection of these layers, may be used. In some embodiments, computation of attributes can be omitted if the training atlases already include the attributes for the atlas image points that are to be used by the machine learning algorithm.

At 604, training module 323 may apply a learning algorithm to generate an anatomical classification model based on the identified image features for the image point. The machine learning algorithm can be a supervised learning algorithm, which seeks to infer a prediction model given a set of training data. For example, the machine learning algorithm for training the structure classifier can be the random forests (RF) machine learning algorithm, which can naturally handle multiple classes, i.e., one classifier to classify several structures. The output of an RF classifier can be a probability estimation of which class the input data belongs to, i.e., which structure the corresponding image point belongs to. At 605, classifier training unit 302 may check if all training samples have been process. If so (605: yes), method 600 may proceed to 606, where classifier training unit 302 outputs the trained classifier model, e.g., to be used by steps 507-508 of method 500. Otherwise (605: no), method 600 may return to 601 to process the next training sample.

Alternative implementations of methods 500 and 600 are contemplated.

In an embodiment, the registered prior day image may be replaced by the current day image for training purpose. Accordingly, the training can be described as:

$$M_n \leftarrow \text{Train}\left\{\bigcup_{j=1}^{n-1}(I_j, S_j^{(j-1)})\right\}, n \geq 2, n = \text{current day}$$

In another embodiments, an exemplary image segmentation process uses prior day images and expert structures or contours C to segment succeeding-days images, without utilizing image registration. The expert drawn or edited contours C are distinguished from the atlas segmentation contours S (e.g., the ABAS structures have been edited by an expert). The exemplary training process of model $M_n$ from the union of data $I_j$, $C_j$ at treatment day n is described below:

$$M_n \leftarrow \text{Train}\left\{\bigcup_{j=1}^{n-1}(I_j, C_j)\right\}, n \geq 2, n = \text{current day}$$

In another embodiment, an exemplary image segmentation process utilizes method 500 disclosed in FIG. 5, but replaces the prior days' ABAS structures S with that day's expert structures C. When the process reaches the last prior day of the patient's prior day images, the method uses ABAS structures from the previous day. The exemplary training process of model RFn is described below.

$$M_n \leftarrow \text{Train}\left\{\bigcup_{j=1}^{n-1}(I_j, C_j), (I_n, S_n^{(n-1)})\right\}, n \geq 2, n = \text{current day}.$$

Learning algorithms other than RF methods may also be used in combination with ABAS segmentations in similar manners as described above. For example, the classifier model may a convolutional neural network model. A convolutional neural network may include a stack of distinct layers that transform an input image into an output structure label map. The layers may form two stages: an encoding stage and a decoding stage. The layers may differ in input size, output size, and the relationship between the input and the output for the layer. Each layer may be connected to one or more upstream and downstream layers in the stack of layers. The performance of a convolutional neural network may thus depend on the number of layers, and the convolutional neural network's complexity may increase as the number of layers increases. A convolutional neural network may be viewed as "deep" if it has more than one stages of non-linear feature transformation, which typically means the number of layers in the network is above a certain number. For example, some convolutional neural networks may include about 10-30 layers, or in some cases more than a few hundred layers. Examples of convolutional neural network models include AlexNet, VGGNet, GoogLeNet, ResNet, etc. These convolutional neural network models can be used at the encoding stage of the full convolutional neural network model.

This present disclosure is not limited to the embodiments discussed above, for other embodiments of training data combinations are possible. Models could be weighted to de-emphasize the population, for instance, or to delete it all together. The individual day's images and structures could be trained in single-image RF models that could later be merged. Other combinations of registered and non-registered sets of images/structures may be possible. In addition, context features may be used in addition to the appearance features described above.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments of the present disclosure illustrated and described herein is not essential, unless otherwise specified.

That is, the operations may be performed in any order, unless otherwise specified, and embodiments of the present disclosure may include additional or fewer operations than those disclosed herein. For example, it is contemplated that executing or performing a particular operation before, contemporaneously with, or after another operation is within the scope of aspects of the present disclosure.

Embodiments of the present disclosure may be implemented with computer-executable instructions. The computer-executable instructions may be organized into one or more computer-executable components or modules. Aspects of the present disclosure may be implemented with any number and organization of such components or modules. For example, aspects of the present disclosure are not limited to the specific computer-executable instructions or the specific components or modules illustrated in the figures and described herein. Other embodiments of the present disclosure may include different computer-executable instructions or components having more or less functionality than illustrated and described herein.

When introducing elements of aspects of the present disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the present disclosure in detail, it will be apparent that modifications and variations are possible without departing from the scope of aspects of the present disclosure as defined in the appended claims. As various changes could be made in the above constructions, products, and methods without departing from the scope of aspects of the present disclosure, it is intended that all matter contained in the above description and shown in the accompanying drawings shall be interpreted as illustrative and not in a limiting sense.

What is claimed is:

1. A system for segmenting medical images, the system comprising:
   a database configured to store a plurality of medical images acquired by an image acquisition device, including one or more first medical images of an object, and a second medical image of the object, each of the one or more first medical images associated with a first structure label map; and
   a processor, configured to:
   register each of the one or more first medical images and the first structure label map to the second medical image to generate a second structure label map;
   train a secondary classifier model using the registered second medical image and the corresponding second structure label map;
   merge the secondary classifier model with a primary classifier model to generate an updated primary classifier model; and
   determine an updated second structure label map associated with the second medical image using the updated primary classifier model.

2. The system according to claim 1, wherein the one or more first medical images include a set of prior day images of the object, the prior day images being images that were acquired prior to an acquisition time of the second medical image.

3. The system according to claim 1, wherein the second medical image is an image of the object taken on a day of a radiotherapy treatment session of a patient.

4. The system according to claim 1, wherein the first structure label map includes expert structure labels identified for each of the one or more first medical images, or wherein the processor is further configured to determine the first structure label map for each of the first medical images using the primary classifier model trained on training images from a population of patients.

5. The system according to claim 1, wherein each of the one or more first medical images and the first structure label map are registered to the second medical image using an atlas-based segmentation method.

6. The system according to claim 1, wherein the primary classifier model is a Random Forests model, or a convolutional neural network model.

7. The system according to claim 1, wherein the processor is further configured to extract at least one feature from the second medical image, and wherein the updated second structure label map is determined by applying the updated primary classifier model to the at least one feature.

8. The system according to claim 7, wherein the at least one feature extracted from the second medical image is extracted from one or more feature maps produced by one or more convolution layers of a convolutional neural network.

9. The system according to claim 1, wherein the one or more first medical images and the second medical image are acquired during serial radiotherapy treatment sessions of a patient, or, wherein the processor is configured to determine the updated second structure label map prior to a radiotherapy treatment delivery.

10. A computer-implemented method for segmenting medical images, the method comprising the following operations performed by at least one processor:
    receiving one or more first medical images of an object, and a second medical image of the object, from a database configured to store a plurality of medical images acquired by an image acquisition device, each of the one or more first medical images associated with a first structure label map;
    registering each of the one or more first medical images and the first structure label map to the second medical image to generate a second structure label map;
    training a secondary classifier model using the registered second medical image and the corresponding second structure label map;
    merging the secondary classifier model with a primary classifier model to generate an updated primary classifier model; and
    determining an updated second structure label map associated with the second medical image using the updated primary classifier model.

11. The method according to claim 10, wherein the one or more first medical images include a set of prior day images of the object, the prior day images being images that were acquired prior to an acquisition time of the second medical image, or, wherein the second medical image is an image of the object taken on a day of a radiotherapy treatment session of a patient.

12. The method according to claim 10, further comprising determining the first structure label map for all the first medical images using the primary classifier model trained on training images from a population of patients.

13. The method according to claim 10, each of the one or more first medical images and the first structure label map are registered to the second medical image using an atlas-based segmentation method.

14. The method according to claim 10, further comprising extracting at least one feature from the second medical image, and wherein the updated second structure label map is determined by applying the updated primary classifier model to the at least one feature.

15. A non-transitory computer-readable medium containing instructions that, when executable by a processor, cause the processor to perform a method for segmenting medical images, the method comprising:
receiving one or more first medical images of an object, and a second medical image of the object, from a database configured to store a plurality of medical images acquired by an image acquisition device, each of the one or more first medical images associated with a first structure label map;
registering each of the one or more first medical images and the first structure label map to the second medical image to generate a second structure label map;
training a secondary classifier model using the registered second medical image and the corresponding second structure label map;
merging the secondary classifier model with a primary classifier model to generate an updated primary classifier model; and
determining an updated second structure label map associate with the second medical image using the updated primary classifier model.

16. The non-transitory computer-readable medium according to claim 15, wherein the one or more first medical images include a set of prior day images of the object, the prior day images being images that were acquired prior to an acquisition time of the second medical image, or, wherein the second medical image is an image of the object taken on a day of a radiotherapy treatment session of a patient.

17. The non-transitory computer-readable medium according to claim 15, further comprising determining the first structure label map for all the first medical images using the primary classifier model trained on training images from a population of patients.

18. The non-transitory computer-readable medium according to claim 15, each of the one or more first medical images and the first structure label map are registered to the second medical image using an atlas-based segmentation method.

19. The non-transitory computer-readable medium according to claim 15, further comprising extracting at least one feature from the second medical image, and wherein the updated second structure label map is determined by applying the updated primary classifier model to the at least one feature.

20. The non-transitory computer-readable medium according to claim 15, wherein the one or more first medical images and the second medical image are acquired during serial radiotherapy treatment sessions of a patient, or, wherein the processor is configured to determine the updated second structure label map prior to a radiotherapy treatment delivery.

* * * * *